United States Patent
Qian et al.

(10) Patent No.: US 7,491,525 B2
(45) Date of Patent: Feb. 17, 2009

(54) SPECIFIC PROLIFERATION IN TUMOUR CELL WHICH CAN EXPRESS ANTIONCOGENE WITH HIGH EFFICIENCY AND THE USE OF IT

(75) Inventors: Qijun Qian, Room 503, A1 Changhai Road 225, Shanghai 200438 (CN); Mengchao Wu, Shanghai (CN); Shuntong Shan, Shanghai (CN)

(73) Assignee: Qijun Qian, Shanghai (CN)

( * ) Notice: Subject to any disclaimer, the term of this patent is extended or adjusted under 35 U.S.C. 154(b) by 248 days.

(21) Appl. No.: 10/483,289

(22) PCT Filed: Jul. 12, 2002

(86) PCT No.: PCT/CN02/00493

§ 371 (c)(1),
(2), (4) Date: Jul. 6, 2004

(87) PCT Pub. No.: WO03/006640

PCT Pub. Date: Jan. 23, 2003

(65) Prior Publication Data

US 2005/0048466 A1 Mar. 3, 2005

(30) Foreign Application Priority Data

Jul. 12, 2001 (CN) ............................. 01 1 26113

(51) Int. Cl.
*C12N 7/01* (2006.01)
*C12N 15/861* (2006.01)
*A61K 48/00* (2006.01)
*A01N 63/00* (2006.01)

(52) U.S. Cl. ................ 435/235.1; 435/320.1; 435/456; 424/93.2; 424/93.6

(58) Field of Classification Search .................... None
See application file for complete search history.

(56) References Cited

U.S. PATENT DOCUMENTS

| 6,432,700 | B1 * | 8/2002 | Henderson et al. ....... 435/320.1 |
| 6,627,190 | B2 * | 9/2003 | Wold et al. ................. 424/93.2 |
| 6,676,935 | B2 * | 1/2004 | Henderson et al. ......... 424/93.2 |
| 7,109,029 | B2 * | 9/2006 | Clarke et al. ................ 435/325 |

FOREIGN PATENT DOCUMENTS

| CN | 1258742 | 7/2000 |
| WO | WO9738013 | 10/1997 |
| WO | WO 00/46355 A2 * | 8/2000 |

OTHER PUBLICATIONS

Evan et al., "A matter of life and cell death," Science 281: 1317-1322, Aug. 28, 1998.*
Yu, De-Chao, et al. (1999) "The Addition of Adenovirus Type 5 Region E3 Enables Calydon Virus 787 to Eliminate Distant Prostate Tumor Xenografts." *Cancer Research* 59, 4200-4203.

* cited by examiner

*Primary Examiner*—Michael Burkhart
(74) *Attorney, Agent, or Firm*—Ladas & Parry LLP

(57) ABSTRACT

The present invention provides a recombinant virus, which highly expresses a cancer therapeutic gene and specifically proliferates in tumor cells, and a method for the proliferation of the same. In said recombinant virus, the transcription of at least one VPEG is under the control of a hTERT promoter, whereby the virus selectively proliferates in telomerase activity positive tumor cells, but substantially not in normal cells negative in the telomerase activity. Said recombinant virus further contains a cancer therapeutic gene inserted in its genome, whereby the cancer therapeutic gene is highly expressed in tumor cells. The tumor cells are killed by the synergistic effects of the virus and the cancer therapeutic gene. Such recombinant viruses can be used to treat various tumors.

16 Claims, 4 Drawing Sheets

(A)

QW1 (Adv-hTERTp-E1a)

(B)

QW2(Adv-hTER-Ep-E1a)

(C)

QW3 (Adv-hTERT-Ep-E1a-HRE-E1b)

(D)

QW2-endostatin(Adv-hTERT-Ep- E1a-endostatin)

SEQUENCE LISTING

<160> NUMBER OF SEQ ID NOS: 27

<210> SEQ ID NO 1
<211> LENGTH: 18
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 1
cgggctccca gtggattc                                                 18

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 2
aacgtggcca gcggcagcac ctc                                           23

<210> SEQ ID NO 3
<211> LENGTH: 39
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 3
ggaattcgcg gccgcagatc tcacagacgc ccaggaacc                          39

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 4
cgggatccat ttaaattggc cggggccagg gcttc                              35

<210> SEQ ID NO 5
<211> LENGTH: 293
<212> TYPE: DNA
<213> ORGANISM: Artificial Sequence
<220> FEATURE:
<223> OTHER INFORMATION: Description of Artificial Sequence: synthetic

<400> SEQUENCE: 5
gaattcgcgg ccgcagatct cacagacgcc caggaccgcg cttcccacgt ggcggaggga    60
ctggggaccc gggcacccgt cctgcccctt caccttccag ctccgcctcc tccgcgcgga   120

```
cccgccccg tcccgacccc tcccgggtcc ccggcccagc cccctccggg ccctcccagc    180
ccctccccct cctttccgcg gccccgccct ctcctcgcgg cgcgagtttc aggcagcgct    240
gcgtcctgct gcgcacgtgg gaagccctgg ccccggccaa tttaaatgga tcc           293

<210> SEQ ID NO 6
<211> LENGTH: 46
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 6
tcgaggacgc acgtgggcgc acgtgggcgc acgtgggatt taaata                    46

<210> SEQ ID NO 7
<211> LENGTH: 46
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 7
agcttattta atcccacgt gcgcccacgt gcgcccacgt gcgcct                     46

<210> SEQ ID NO 8
<211> LENGTH: 327
<212> TYPE: DNA
<213> ORGANISM: Artificial Sequence
<220> FEATURE:
<223> OTHER INFORMATION: Description of Artificial Sequence: synthetic

<400> SEQUENCE: 8
gaattcgcgg ccgcagatct cacagacgcc caggaccgcg cttcccacgt ggcggaggga    60
ctggggaccc gggcacccgt cctgccccct caccttccag ctccgcctcc tccgcgcgga    120
ccccgccccg tcccgacccc tcccgggtcc ccggcccagc cccctccggg ccctcccagc    180
ccctccccct cctttccgcg gccccgccct ctcctcgcgg cgcgagtttc aggcagcgct    240
gcgtcctgct gcgcacgtgg gaagccctgg ccccggccac tcgacgcacg tgggcgcacg    300
tgggcgcacg tgggatttaa ataagct                                        327

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 9
ttcaagaatt ctcatgtttg                                                 20

<210> SEQ ID NO 10
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 10
atttaaatct cgagtcgaca ctagtgcggc cgcttcgaac cggtgtcgga gcggctcgga    60
```

```
<210> SEQ ID NO 11
<211> LENGTH: 70
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 11
accggttcga agcggccgca ctagtgtcga ctcgagattt aaatccggtg actgaaaatg     60
agacatatta                                                           70

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 12
ttctctagac acaggtgatg                                                 20

<210> SEQ ID NO 13
<211> LENGTH: 175
<212> TYPE: DNA
<213> ORGANISM: Artificial Sequence
<220> FEATURE:
<223> OTHER INFORMATION: Description of Artificial Sequence: synthetic

<400> SEQUENCE: 13
ccacagtgca tacgtgggct ccaacaggtc ctcttccaca gtgcatacgt gggctccaac     60
aggtcctctt ccacagtgca tacgtgggct ccaacaggtc ctcttccaca gtgcatacgt    120
gggctccaac aggtcctctt ccacagtgca tacgtgggct ccaacaggtc ctctt         175

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: synthetic

<400> SEQUENCE: 14
ggtaggcgtg tacggtggga ggtctatata agcagagctc gtttagtgaa ccgtcagatc     60

<210> SEQ ID NO 15
<211> LENGTH: 247
<212> TYPE: DNA
<213> ORGANISM: Artificial Sequence
<220> FEATURE:
<223> OTHER INFORMATION: Description of Artificial Sequence: synthetic

<400> SEQUENCE: 15
actagtccac agtgcatacg tgggctccaa caggtcctct tccacagtgc atacgtgggc     60
tccaacaggt cctcttccac agtgcatacg tgggctccaa caggtcctct tccacagtgc    120
atacgtgggc tccaacaggt cctcttccac agtgcatacg tgggctccaa caggtcctct    180
tggtaggcgt gtacggtggg aggtctatat aagcagagct cgtttagtga accgtcagat    240
cactagt                                                              247
```

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 16
tcacctgtgt ctagagaatg c                                         21

<210> SEQ ID NO 17
<211> LENGTH: 43
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 17
ctcccaagcc tccatactag tttaaacatt atctcaccct tta                 43

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 18
actagtatgg aggcttggga gtgtttg                                   27

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 19
ggccagaaaa tccagcaggt a                                         21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 20
aggtctatat aagcagagct c                                         21

<210> SEQ ID NO 21
<211> LENGTH: 63
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 21
ggggaattca ccatgggggt actgctcaca cagaggacgc tgctcagtct ggtccttgca  60
ctc                                                             63

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 22
ctgctcagtc tggtccttgc actcctgttt ccaagcatgg cgagccaccg cgacttccag        60

<210> SEQ ID NO 23
<211> LENGTH: 65
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 23
gctctagact attacttgga ggcagtcatg aagctgttct caatgcatag cacgatgtag        60
gcgtg                                                                   65

<210> SEQ ID NO 24
<211> LENGTH: 641
<212> TYPE: DNA
<213> ORGANISM: Artificial Sequence
<220> FEATURE:
<223> OTHER INFORMATION: Description of Artificial Sequence: synthetic

<400> SEQUENCE: 24
gaattcacca tgggggtact gctcacacag aggacgctgc tcagtctggt ccttgcactc        60
ctgtttccaa gcatggcgag ccacagccac cgcgacttcc agccggtgct ccacctggtt       120
gcgctcaaca gcccctgtc aggcggcatg cggggcatcc gcggggccga cttccagtgc       180
ttccagcagg cgcggggccgt ggggctggcg ggcaccttcc gcgccttcct gtcctcgcgc      240
ctgcaggacc tgtacagcat cgtgcgccgt gccgaccgcg cagccgtgcc catcgtcaac       300
ctcaaggacg agctgctgtt tcccagctgg gaggctctgt tctcaggctc tgagggtccg       360
ctgaagcccg gggcacgcat cttctccttt aacggcaagg acgtcctgag gcaccccacc       420 tggcccccaga agagcgtgtg gcatggctcg gaccccaacg ggcgcaggct gaccgagagc       480
tactgtgaga cgtggcggac ggaggctccc tcggccacgg gccaggcctc ctcgctgctg       540
gggggcaggc tcctggggca gagtgccgcg agctgccatc acgcctacat cgtgctatgc       600
attgagaaca gcttcatgac tgcctccaag taatagtcta g                           641

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 25
tggccggggc cagggcttc                                                    19

<210> SEQ ID NO 26
<211> LENGTH: 22
<212> TYPE: DNA
<213> ORGANISM: Artificial Sequence -continued

```
<220> FEATURE:
<223> OTHER INFORMATION: Description of Artificial Sequence:
      oligonucleotide

<400> SEQUENCE: 26
agcacgatgt aggcgtgatg gc                                               22

<210> SEQ ID NO 27
<211> LENGTH: 6
<212> TYPE: DNA
<213> ORGANISM: Artificial Sequence
<220> FEATURE:
<223> OTHER INFORMATION: Description of Artificial Sequence:
      oligonucleotide

<400> SEQUENCE: 27 cacgtg                                                                  6
```

SPECIFIC PROLIFERATION IN TUMOUR CELL WHICH CAN EXPRESS ANTIONCOGENE WITH HIGH EFFICIENCY AND THE USE OF IT

TECHNICAL FIELD

This invention relates generally to a recombinant virus. More specifically, the invention relates to a virus which highly expresses a cancer therapeutic gene and specifically propagates in tumor cells, and the use thereof.

BACKGROUND ART

Malignant tumors severely threat the human life. At present, the conventional means for the treatment of malignant tumors are surgery, radiotherapy and chemotherapy, which, however, cannot achieve satisfactory effect on most tumors. The therapeutic index of most chemotherapeutics is very low, that is, their therapeutic dose and toxic dose are almost the same. Thus the aforementioned therapeutic means are accompanied with substantive toxic effect, including the life-threatening suppression of bone marrow. Therefore, it is very important for tumor treatment to develop methods which selectively kill the tumor cells but not affect the normal cells. These methods mainly rely on the characteristic marker of tumor cells, and their therapeutic effects depend on whether said tumor marker is strictly restricted to tumor cells.

Telomere is a structure of eukaryotic cells, which protects the end of chromosomes. The telomere of normal cells shortens by 50-200 nucleotides after each cell division. When the length of the telomere decreases to a certain degree, the cells will die. While in malignant cells, the telomerase is activated, whereby elongating the shortened telomere and maintaining the stability of the chromosome. Then the cells escape from death and become immortal. It means that the tumor cells can propagate continuously. Therefore, the activation of telomerase plays an essential role in the onset and development of tumor. The telomerase activity is positive in about 90% tumor cells, while it is negative in most of the normal cells. Based on this fact, the telomerase can be used as a characteristic marker of tumor cells.

At present, the telomerase in human is known to be consisted of the following three components: (1) RNA component (hTERC), which acts as an endogenous template for repeated synthesis of telomere; (2) telomerase binding protein (TEP1); and (3) telomerase catalytic subunit (abbreviated as hTERT), also named as telomerase reverse transcriptase. RNA component and hTERT are essential for the activity of telomerase. Recent study further shows that hTERT plays a critical role in the telomerase activity, and is highly expressed in most tumor cells or tumor cell lines, while is expresses at a lower level or even not expressed in normal cells. Thus it is believed that the promoter of hTERT is in an activated state in most tumor cells.

Various researches have been carried out on tumor therapy, which aims at using telomerase as the target. These studies include the following: (1) tumor therapy, which aims to inhibit telomerase activity; (2) gene therapy, which uses telomerase promoter (i.e. hTERT promoter and/or telomerase RNA component promoter) to drive an apoptosis gene or suicide gene; and (3) virotherapy, which employs a tumor-specific propagating virus controlled by the hTERT promoter.

However, the aforementioned therapy still has significant defects. Firstly, the telomerase activity is negative in about 10% of the human tumors. In these tumor cells, the length of the telomere is maintained by the mechanism termed as Alternative Lengthening of Telomere (ALT). Furthermore, due to the heterogenicity of tumor cells, the fact that the telomerase activity is positive in certain tumor cells of a patient does not means that the telomerase activity is positive in all of the tumor cells in said patient. ALT mechanism may also exist in said patient. Thus antitumor strategy only aiming at the telomerase cannot kill all the tumor cells. Studies have shown that, telomerase inhibitor can inhibit the telomerase activity, but also enhance ALT mechanism in tumor cells, whereby not being efficient to kill the tumor cells. Secondly, in human body, the telomerase activity is also positive in germ celler, hemopoietic stem cells and diverticulum cells in the gastrointestinal tract. Thus the tumor therapy aiming at the telomerase may cause toxicity to said cells.

In the last decade, gene therapy was developed in clinical research. Clinical practice shows that, gene therapy is very safe, but its efficiency in treating tumor is also very low, and in some cases, it even has no therapeutic effect. Although there are various reasons for said defect, the main reasons are lower efficiency of in vivo transfection of the vector system, lower expression of the cancer therapeutic gene and being unable to target tumor cells. Thus the cancer therapeutic gene cannot be transfected to sufficient tumor cells and be highly expressed in said cells, which adversely affects the therapeutic effect of gene therapy in tumor clinical practice. It is a key point in tumor gene therapy that how to increase the transfection efficiency of the vector system, how to increase the expression of the cancer therapeutic gene and the specificity to tumor cells.

In recent years, due to the rapid development in virology, molecular biology and oncology, the genomes of various virus have been sequenced, and their gene structures and functions have been studied in detail, thus virus genes can be effectively modified. The modified virus has enhanced ability to transfect tumor cells, replicate in cells as well as increased lysis effect. Whereas, in normal cells, said ability is decreased or even lost. Thus such virus can replicate selectively in tumor cells, and propagate to thousands or even millions folds, causing tumor cell lysis. Upon cell lysis, new virus is released, and again transfects and propagates in tumor cells, until all the tumor cells are killed. Since such virus cannot propagate in normal cells, it has little effect on them. Such virus, which specifically propagates in tumor cells, is termed as tumor-specific propagating virus. As yet, about ten types of tumor-specific propagating virus are in clinical test.

However, virotherapy, which only employs a tumor-specific replicating virus, has its own limits. Firstly, due to the complicated mechanism of tumor formation, and The heterogenicity of tumors, there is obvious difference among patients, tumors or even cells in a tumor, With regard to the telomerase, the fact that the telomerase activity is positive in certain tumor cells of a patient does not mean that the telomerase is positive in all the tumor cells of said patient. Thus the virus employing a certain tumor mechanism to propagate cannot kill all the tumor cells. Secondly, the diffusion of virus may be inhibited by various factors in tumors, such as fibrosis, existence of normal cells and necrosis region. Thirdly, in certain tumors, the insufficient expression of the receptor of the virus (e.g. Coxsackie virus receptor) inhibits the infection of said virus. Fourthly, the immune response of the patient to the viruses also inhibits the proliferation and diffusion of virus.

ONYX Pharmaceutical Company (USA) applied only E1b 55 kDa protein deleted virus (ONYX-015) to treat tumor, but only achieved 15-20% efficiency in clinics (Nemunaitis, J. et al, Cancer Res., 2000, 60(22):6359; U.S. Pat. No. 5,677,178; and U.S. Pat. No. 5,801,029).

SUMMARY OF THE INVENTION

The present invention provides a recombinant virus, wherein the transcription of at least one of the virus proliferation essential gene (VPEG) is under the control of a telomerase promoter, and wherein the genome of said virus comprises a nucleotide sequence of an antitumor gene.

In one embodiment, said telomerase promoter is selected from the group consisting of hTERT promoter and the telomerase RNA component promoter.

Where hTERT promoter is used, several copies of E-box sequence (5'cacgtg 3'(SEQ ID NO:27)) are added downstream of the transcription initiation site. The recombinant virus of this invention may additionally have the following features:
1) transcription of other VPEG is under the control of a cis-acting element specifically activated in tumor cells; and/or
2) at least one VPEG is inactivated, while the virus can still specifically propagate in tumor cells.

The present invention also provides a method, by using said recombinant virus, to treat tumors in mammalian, especially in human, which method comprises: 1) infecting tumor cells in vitro or in vivo using said virus; and 2) the virus selectively replicates and propagates essentially in tumor cells, resulting in the increase of the copies of the nucleotide sequences of a cancer therapeutic gene and the increase of the expression of the cancer therapeutic gene in tumor cells, thereby inhibiting the formation, growth and metastasis of the tumors. Appropriately, said method may also comprise administering chemical antitumor drugs before, during and/or after the infection of tumor cells.

The present invention also relates to the use of said recombinant virus to inhibit the growth of tumor cells.

Furthermore, the present invention relates to the use of said recombinant virus in the preparation of drugs for treating tumor.

DETAILED DESCRIPTION OF THE INVENTION

Figure 1:
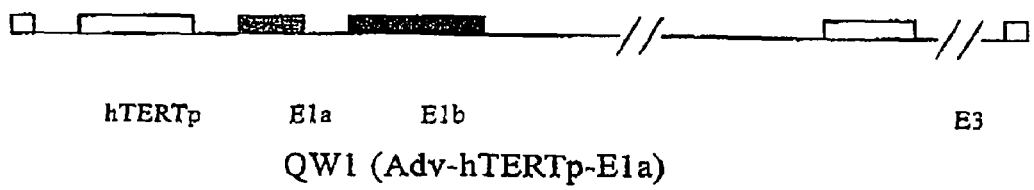
FIG. 1 shows the structure of the viruses QW1(Adv-hTERTp-E1a), QW2(Adv-hTER-Ep-E1a), QW3(Adv-hTERT-Ep-E1a-HRE-E1b) and QW2-endostatin(Adv-hTERT-Ep-E1a-endostatin). QW1(Adv-hTERTp-E1a) represents an attenuated reproductive adenovirus with hTERT promoter controlling the expression of E1A. QW2 (Adv-hTER-Ep-E1a) represents an attenuated reproductive adenovirus comprising a hTERT promoter and three copies of E-box sequence incorporated downstream thereof to control the expression of E1A. QW3(Adv-hTERT-Ep-E1a-HRE-E1b) represents an attenuated reproductive adenovirus comprising a hTERT promoter and three copies of E-box sequence incorporated downstream thereof to control the expression of E1A, and hypoxia response element(HRE) in combination with minimal human cytomegalovirus promoter to control the expression of E1B. QW2-endostatin(Adv-hTERT-Ep-E1a-endostatin) represents an attenuated reproductive adenovirus comprising an endostatin gene, a hTERT, and three copies of E-box sequence incorporated downstream thereof to control the expression of E1A.
Figure 1:
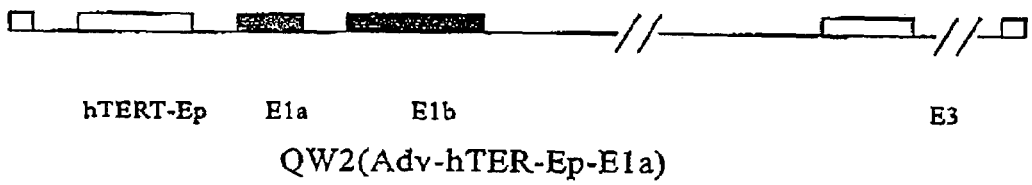
Figure 1:
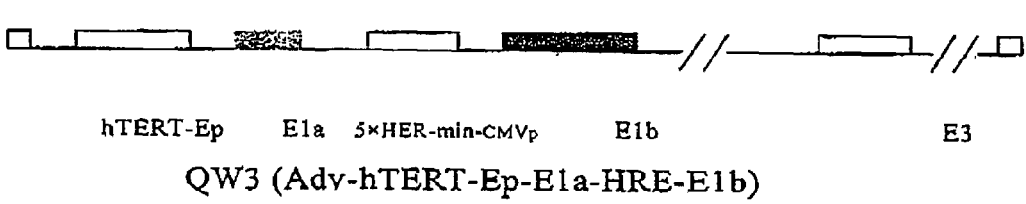
Figure 1:
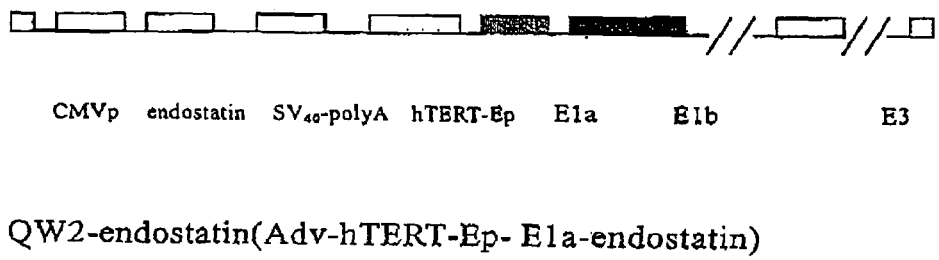

As described above, the present invention relates to a recombinant virus, wherein the expression of at least one VPEG of the virus is under the control of a telomerase promoter, and wherein the genome of said virus comprises a nucleotide sequence of a gene which functions to treat tumors.

The telomerase activity is positive in about 90% tumor cells, while it is negative in most normal cells. Based on this fact, the telomerase can be used as a characteristic marker of tumor cells. At present, the telomerase in human is known to be consisted of the following three components: (1) RNA component (hTERC), which acts as an endogenous template for repeated synthesis of telomere; (2) telomerase binding protein (TEP1); and (3) telomerase catalytic subunit (abbreviated as hTERT), also named as telomerase reverse transcriptase. RNA component and telomerase catalytic subunit are essential for telomerase activity. Recent study further shows that hTERT plays a critical role in the telomerase activity, and is highly expressed in most tumor cells or tumor cell lines, while is expressed at a lower level or even not expressed in normal cells. Thus it is believed that the hTERT promoter and the telomerase RNA component promoter are in an activated state in most tumor cells.

Recently, the cis-acting elements of TERT gene have been cloned respectively from human and mouse. Their GC contents are high, with the TATA box and CAAT box absent. They also comprise binding sites for various transcription factors, including transcriptional activators (Myc and SP1) and transcriptional inhibitors (Mad1, p53 and MZF2). The activity of human hTERT promoter has been studied through truncating said promoter from the 5' end and constructing promoter deletion mutants of various lengths. The results show that a promoter core region of at least 1bp exists upstream of the transcription initiation site, which region is very important for the activity of said promoter. The core region of hTERT promoter contains E-box (CACGTG) and a binding site for SP1. Although the expression of SP1 transcriptional factor is up-regulated in somatic cells negative in the telomerase activity, and the binding of SP1 to its binding site promotes the transcription initiation of hTERT gene, yet the most critical factors regulating the transcription and expression of hTERT gene are those which bind to the E-box, such as Myc, Mad1 and the like. High expression of Myc protein can substantively increase the activity of hTERT promoter, whereby promoting gene transcription and enhancing telomerase activity. Besides the E-box (−187 bp~−182 bp) upstream of the transcription initiation site, another E-box (+22 bp~+27 bp) is present downstream of the transcription initiation site of hTERT gene and upstream of the translation initiation site. This downstream E-box can bind respectively to Myc and Mad1, whereby activating and inhibiting the transcription of hTERT, respectively. Recent studies show that the E-box downstream of the transcription initiation site of hTERT promoter is a target site of the negative regulation in telomerase negative cells. We found that, through inserting copies of E-box to downstream of the transcription initiation site, the activity of hTERT promoter can be substantively inhibited in telomerase negative cells, while in telomerase activity positive cells, said E-box may be a positive regulation site which binds to an activator such as USP (Upstream stimulatory factor) of Myc family and which activates the transcription of the hTERT gene. Through the above-described study, it is also found that, a silencer of about 400 bp (−776 bp~−378 bp) is present upstream of the core region of hTERT promoter. Said silencer contains several MZF2 (Myeloid-specific zinc finger protein 2) binding motifs. Mutations introduced into these sites result in transcriptional activation of hTERT gene, while overexpression of MZF2 as well as its interaction with the binding motif down-regulates the transcription of the hTERT gene and decreases the telomerase activity. Experiments showed that the silencer upstream of the core region of hTERT promoter is a negative control region of hTERT gene, and MZF2 is a negative regulator of hTERT gene. MZF2 is expressed not only in bone marrow cells, but also in cell lines derived from different tissues, indicating that MZF2 ubiquitously and negatively regulates hTERT gene. It can be concluded that, the expression of hTERT gene and the activity of telomerase are controlled strictly by various factors, including activators and inhibitors, and that the main site for regulation is located in the promoter region of the hTERT gene.

The regulation of the activation of gene transcription is affected by the interaction between a trans-acting factor (i.e. transcription factor) and a cis-acting element. The absence or presence of certain transcription factors will affect the transcription levels of genes. The promoters of hTERT and of telomerase RNA component are specifically activated in the cells with telomerase activity, and the genes under control of said promoters are transcribed. The present invention uses the promoter of hTERT or of telomerase RNA component to control genes essential for the proliferation and propagation of the virus, and thus the VPEG express only in said telomerase positive cells, whereby the virus propagating only in said positive cells, and hardly propagating in telomerase negative cells. Such modified viral vectors can be used to kill special target cells positive in the telomerase activity in cell mixtures. The modified virus selectively propagates in and kills said target cells. When the modified virus is mixed with cell mixtures in vivo or in vitro, it proliferates and propagates only in target cells. In other words, other cells will not be killed by this virus due to the selective proliferation of virus in the target cells. Once the target cells are killed, the virus will not propagate any more.

In one embodiment, said telomerase promoter is selected from the group being consisted of hTERT promoter and the telomerase RNA component promoter.

Where hTERT promoter is used, several copies of the E-box sequence (SEQ ID NO:27) can be introduced downstream of the transcription initiation site.

The region essential for the proliferation of the virus according to the invention varies with the virus used, and it is known to those skilled in the ar The term "the transcription of at least one VPEG of the virus is under the control of a telomerase promoter" refers to the relative positions of VPEG and the telomerase promoter in the virus genome. Said relative position may be varied, provided that the transcription of said VPEG can be controlled effectively by the telomerase promoter. In one embodiment, the telomerase promoter contained in said virus may be suitably positioned upstream of the transcription initiation site of VPEG. In another embodiment, the telomerase promoter may replace the endogenous promoter of the virus. In yet another embodiment, the recombinant virus may comprise at least one telomerase promoter between the transcription initiation site and the translation initiation site of VPEG.

The reproductive recombinant virus of this invention, which can specifically kill the telomerase positive tumor cells, comprises at least one VPEG under the control of a telomerase promoter. The, telomerase promoter is inserted between the transcription initiation site and the translation initiation site of VPEG. Said telomerase promoter is activated in telomerase positive tumor cells, while inactivated in normal cells negative in telomerase activity. Said telomerase promoter comprises at least one of the following components: the telomerase reverse trascriptase promoter and the telomerase RNA component promoter. The above-described VPEG is an early gene of the virus, such as an immediate early gene of herpes simplex virus (ICE4).

In the present invention, adenoviruses can be used. VPEG may be selected from the group being consisted of the following adenoviral early genes: E1A, E1B, E2 and E4, or may be a late gene.

Human adenovirus can be divided into six subgenus, which are A, B, C, D, E and F, respectively. They are different in their ectotropism to host cells, tumorigenicity and pathogenic history. Adenoviral genes can be classified into two groups, namely early genes and late genes. The early gene includes E1A, E1B, E2 and E4.

E1A expresses immediately (0-2 hr) after virus infection, and is the first expressed adenoviral protein. E1A acts as a trans-activating transcriptional regulator, and is essential for the expression of other viral early gene. E1A also trans-activates other viral promoters. Therefore, if the expression of E1A is absent, the gene product essential for the proliferation of adenovirus DNA cannot be produced, and thus the adenovirus is not able to replicate and propagate.

The transcription of E1B is activated by E1A protein. E1B protein is essential for the transportation of late gene mRNA from nucleus to cytoplasm. The absence of E1B expression will lead to lower expression of the viral late genes and will be unable to close the endogenous protein synthesis of the host cell.

E4 gene locates at the right end of the virus genome. Its open-reading frame 3 (ORF3) and ORF6 can increase the mRNA levels of adenoviral main late genes. The titer of the mutant virus lack of the function of ORF3 and ORF6 is $10^6$ folds lower than that of the wild virus.

In another embodiment, the invention provides a recombinant virus which has one of the following cancer therapeutic genes inserted into the viral genome: (1) cancer suppressor gene; (2) antiangiogenic gene; (3) cytokine gene; (4) prodrug convertase gene; and (5) apoptosis gene.

In one embodiment, the cancer therapeutic gene in said recombinant virus according to this invention is a cancer suppressor gene, which inhibits the growth of tumor cells. Said cancer suppressor gene may be selected from, but not limited to P53, Rb, NF1, VHL and APC.

In one embodiment of this invention, the cancer therapeutic gene of said recombinant virus according to this invention is a antiangiogenic gene, which inhibits neo-vascularization in tumors and blocks the nutrition supply to tumor cells, leading to tumor cell death and significant atrophy and even regression of the tumor. Furthermore, if neo-vascularization in tumors is suppressed, the pathway of tumor metastasis is also blocked. The antiangiogenic gene may be selected from, but not limited to endostatin gene, angiogenesis inhibitor gene, kringle1-4 structure, kringle1-5 structure, kringle1-3 structure and kringle1-5 structure plus kringle1-3 structure of plasminogen, interferon-α gene, interferon-β gene, interferon-γ gene, thrombospondin gene, platelet factor 4 gene, plasminogen activator inhibitor (PAI) gene, interleukin 12 and fibronectin gene.

Optionally, an antiangiogenis inhibitor may comprise a nucleotide sequence encoding a secretory signal peptide. Said secretory signal peptide may be endogenous or exogenous, and may be selected from, but not limited to a signal peptide of the antiangiogenis inhibitors, a signal peptide from M-tumorigenic protein and a signal peptide from immunoglobulin K chain.

In one embodiment of this invention, the cancer therapeutic gene of said recombinant virus according to this invention is a cytokine gene. Cytokine can activate the immune cells and enhance haemopoiesis. Said cytokine may be selected from, but not limited to interleukin 2, interleukin 12, granulocyte-monocyte colony stimulating factor, tumor necrosis factor, interferon α, interferon β, interferon γ, Light and F1t3 ligand.

In one embodiment of this invention, the cancer therapeutic gene of said recombinant virus according to this invention is a prodrug convertase gene, which converts a non-toxic drug into a toxic drug and thus stimulates the killing of tumor cells. Said prodrug convertase gene may be selected from, but not limited to herpes simplex virus thymidine kinase, varicella-zoster virus thymidine kinase and E. coli cytosine deaminase.

In one embodiment of this invention, the cancer therapeutic gene of said recombinant virus according to this invention is an apoptosis gene, which induces the apoptosis of eukaryotic cells. Said apoptosis gene may be selected from, but not limited to ICE, capase-3, capase-8 and capase-9.

When the virus replicates in tumor cells, the copies of the cancer therapeutic gene increase, leading to the high expression of the cancer therapeutic gene in the tumor cells.

The recombinant virus provided in this invention may additionally has the following features:
1) transcription of other VPEG is under the control of a cis-acting element specifically activated in tumor cells; and/or
2) at least one other VPEG is inactivated, while the virus can still specifically propagate in tumor cells.

Regions essential for virus proliferation according to the invention vary from virus to virus, and it is generally known to those skilled in the art. The term "the transcription of the VPEG is under the control of a cis-acting element specifically activated in tumor cells" refers to the relative position of VPEG and the cis-acting element specifically activated in tumor cells in the virus genome. Said relative position may be varied from virus to virus, provided that the transcription of said VPEG can be controlled effectively by the cis-acting element specifically activated in tumor cells. In one embodiment, the cis-acting element specifically activated in tumor cells contained in said virus may be suitably positioned upstream of the transcription initiation site of VPEG. In another embodiment of this invention, the cis-acting element specifically activated in tumor cells may replace the endogenous promoter of the virus. In yet another embodiment of this invention, the recombinant virus may comprises, between the transcription initiation site and translation initiation site of VPEG, at least one cis-acting element specifically activated in tumor cells.

In one embodiment, the recombinant virus is a herpes simplex virus, of which the VPEG comprises the immediate early gene ICP4. In another embodiment, the recombinant virus is an adenovirus, of which the VPEG may be any of the following adenoviral early genes E1A, E1B, E2, or E4, or may be adenoviral late gene.

In one specific embodiment, the cis-acting element in the recombinant virus according to this invention may be selected from, but not limited to Hypoxia response element, S phase specific promoter (E2F promoter), α-fetoprotein enhancer and promoter, carcino-embryonic antigen enhancer and promoter, tyrosinase enhancer and promoter, urokinase-type plasminogen activator enhancer and promoter, ErbB2 enhancer and promoter, ErbB3 enhancer and promoter, ErbB4 enhancer and promoter, DF3 breast cancer-associated antigen enhancer, prostaglandin specific antigen enhancer and promoter, vasodilatin enhancer and promoter, Orip from EB virus, FR enhancer of Orip from EB virus, and Bam HI C-promoter of EB virus.

Hypoxia Response Element (HRE)

With the proliferation of tumor cells, the oxygen consumption of tumor cells will continuously increase, resulting in hypoxia in solid tumors. Most solid tumors highly express a transcription factor namely, hypoxia inducing factor-1 α (HIF-1 α), which binds to HRE and promotes its transcription. Thus HIF-1 α can activate the transcription of HRE in solid tumor. HRE may be derived from angiogenesis factor promoter, erythropoietin promoter, glucose transporter protein 1 promoter, heme oxygenase promoter and inducible NO synthase promoter.

S Phase Specific Promoter (E2F-1 Promoter)

E2F-1 is a growth regulation gene widely expressed in various tissues. Its expression is associated with cell cycle, and the transcription level peaks in S phase. RB protein and other members of the RB family can bind to E2F-1 to form a specific complex, whereby inhibiting its capacity of activating transcription. Thus E2F-1 is down-regulated by RB. In many tumor cells, due to the abnormality in Rb/P16INK4 α/cyclin D signal transduction pathway, E2F-1 is highly expressed, and E2F-1 cis-acting element is in an activated state in most tumor cells.

α-fetoprotein(AFP) Enhancer and Promoter

AFP is a carcino-embryonic protein, and its expression is mainly restricted to the differentiated tissues (i.e. yolk sac, fetal liver and viscera) originated from the endoderm. The expression of AFP varies with the tissue type and the developmental stage. AFP attracts the attention of the researchers in clinic, because the serum level of AFP is increased in most liver cancer patients. It should be noted that, the serum level of AFP is also increased in the patients at the later stage of some diseases. The study shows that, the increase of AFP level in serum is caused by the expression of AFP in liver cancer cells, while in the normal tissues surrounding the liver cancer cells, the expression of AFP is undetected. Thus the expression of AFP is a characteristic of liver cancer cells.

It is reported in the publication that, AFP transcription cis-acting element is sensitive to the proteins associated with AFP-producing cells (e.g. transcription factor, cofactor like AFP binding protein). The transcription cis-acting element shall comprise at least one AFP promoter and one AFP enhancer. The cell specific transcriptional cis-acting element derived from AFP gene has been identified. An AFP control region (including promoter, putative silencer and enhancer) exists upstream of the transcription initiation site at 5' end.

In human AFP control region, AFP enhancer locates between −3954 nt and −3335 nt, and AFP promoter locates between −174 nt and +29 nt (all relative to the transcription initiation site). Juxtaposition of these two elements results in an AFP transcription cis-acting element possessing full functions. Ido, et al. described a promoter fragment of about 259 bp (nt −230~+29) specifically expressed in liver cancer cells. AFP enhancer locates between −3954 nt and −3335 nt, and comprises two regions which are named as A and B respectively. The promoter region comprises the typical TATA box and CAAT box. AFP transcription regulation element preferably contains one enhancer region, more preferably two enhancer regions.

AFP transcription cis-acting element may contain any number of structural elements, and not limited to one promoter and one enhancer, It may contain one AFP enhancer in combination with one AFP promoter, or one AFP promoter in combination with one heterologous enhancer, or a heterologous promoter in combination with an AFP enhancer, or multiple combinations of said elements. The promoter and enhancer of AFP transcription cis-acting element may be positioned in any orientation and in any distance relative to the gene of interest, provided that the cell specific transcription activity of AFP is maintained. The current adenovirus vector may additionally comprise an endogenous silencer of AFP transcription cis-acting element, which may also be deleted.

Carcino-Embryonic Antigen (CEA) Enhancer and Promoter

CEA is a tumor-associated glucoprotein antigen of 18,000 Da, and is mainly present in tumors originated from endoderm of gastrointestinal tract, such as colon and rectum cancer, gastric carcinoma and carcinoma of pancreas. CEA is also present in other adenocarcinoma such as breast cancer, and in lung cancer. Since CEA can be detected in the circulatory system of many patients with CEA-positive tumor, CEA attracts the attention of the researchers in clinic. In about 50% cases of the lung cancer, CEA can be detected in the circulatory system. The level of CEA in adenocarcinoma is over 20 ng/L. In about 50% of the patients suffering from gastric carcinoma, serum CEA is positive.

The 5'-terminal sequence of CEA exhibits a cell-specific activity. CEA promoter region is located in the first 424 bp region upstream of the transcription initiation site at 5' end, and exhibits a cell-specific activity, as its promoter activity is higher in CEA-producing cells than in CEA-non-producing Hela cells. Furthermore, a cell-specific enhancer has also been found (see PCT/GB/02456). It appears that the CEA promoter, putative silencer and enhancer are located within the 14.5 Kb region from the transcription initiation site. Further research on the 5' terminal region of CEA reveals that, two regions upstream of the transcription initiation site (−13.6 kb~−10.7 kb, and −6.1 kb~−4.0 kb, respectively), when linked with polymerized promoters, will increase the expression level of a reporter gene in CEA-producing Lovo and SW1463 cell lines with specificity. Richard, et al. also located the promoter within the region from −90 bp to +69 bp from transcription initiation site, wherein the sequence of 41 bp~−18 bp is essential for the expression. PCT/GB/02546 described a series of 5'-terminal fragments exibiting cell-specificity, which included the following sequences: nt−299~nt+69, nt−90~nt+69, nt−13600~nt−10600, and nt−6100~nt−3800 (all relative to the transcription initiation site). In addition, the fragment of nt−402~nt +69 in CEA gene can also render the transcription of the linked gene to be tissue-specific. CEA cis-acting elements mentioned herein to be used in vectors are derived from mammalian cells, including but not limited to human cells. Thus any CEA cis-acting element can be used, provided that the essential functional region is maintained in the vector.

Tyrosinase Enhancer and Promoter

Human tyrosine gene has a cis-acting element directing the specific expression in melanocytes. Said element comprises a tyrosinase distal element (TDE) of about 20 bp, containing a sequence of CATGTG located −1874~−1835 bp from the transcription initiation site. A promoter comprising −209 bp~+61 bp of human tyrosinase gene is found to be able to direct the specific expression of genes in melanocytes. Similarly, a similar sequence located 5' terminal of the mouse tyrosinase gene is also registered in GenBank. The minimal promoter of mouse TRP-1 gene has been identified, which comprises the sequence of −44 bp~+107 bp from the transcription initiation site.

In some examples, the melanocyte-specific transcription regulation element derived from the 5' terminal of human tyrosinase gene comprises the sequence of nt−231~nt+65, or the sequence of nt−1956~nt−1716, from the transcription initiation site. Said melanocyte-specific transcription regulation element can also comprise a said two sequences juxtaposed together. It is reported that, the sequence of nt−1956~nt−1716 from the transcription initiation site of human tyrosinase gene has a synergistic action on the specific expression of operably linked reporter gene in melanocytes under the control of a homologous or heterologous promoter. Therefore, in some examples, melanocyte-specific transcription regulation element comprises a heterologous promoter operably linked to the sequence of nt−1956~nt−1716.

Urokinase-Type Plasminogen Activator (uPA) Enhancer and Promoter uPA protein and its receptor uPAR are expressed in most common tumors, and play an important role in tumor metastasis. They are associated with breast cancer, rectal cancer, prostate cancer, liver cancer, lung cancer and uterus cancer. The transcriptional cis-acting elements of uPA and uPAR have been extensively studied.

ErbB2 Enhancer and Promoter

ErbB2 enhancer and promoter are specifically activated in breast cancer cells. C-erbB2/neu gene is a transforming gene, which encodes a trans-membrane protein of 185 kDa associated with epidermal growth factor receptor. In human, C-erbB2/neu is expressed during the fetal development. C-erbB2/neu protein can hardly be detected by immunohistochemical method in normal adult epithelia. Over expression and amplification of C-erbB2/neu is associated with many human tumors, such as breast cancer, oophoroma, uterus cancer, prostate cancer, gastric carcinoma and lung cancer. The effect of the overexpression of C-erB2/neu has been sufficiently studied in breast cancer and oophoroma. It is showed that, C-erbB2/neu is overexpressed in 20-40% breast cancer and 30% oophoroma, and is associated with the poor prognosis of these two diseases.

C-erbB2/neuTREs of human, rat and mouse have been identified, which show specific transcription activity in C-erbB2/neu expressing cells.

ErbB2 enhancer and promoter are specifically activated in breast cancer cells.

ErbB4 enhancer and promoter are specifically activated in breast cancer cells and in gastric carcinoma cells.

DF3 Breast Cancer-associated Antigen (MUC1) Enhancer

DF3 breast cancer-associated antigen (MUC1) enhancer is specifically activated in beast cancer cells. The protein products of MUC1 gene (e.g. mucoprotein, MUC1 protein, epithelial sialoprotein, polymorphous epimucin or PEM, EMA, DF3 antigen, NPGP, PAS-O or CA15.3 antigen) are generally expressed in the apexes of the epithelial cells in the glands and ductus of mammary gland, as well as stomach, pancreas, lung, trachea, kidney, uterus and salivary gland. In 75-90% human breast tumors, mucoprotein is found to be over expressed. The regulation of mucoprotein expression is associated in some degree with the differentiation of the breast tumors.

It appears that the overexpression of MUC1 gene in human breast cancer cell lines MCF-7 and 2R-75 is in the transcriptional level. The regulatory sequence of MUC1 gene, including a sequence 0.9 kb upstream of the transcription initiation site, has been cloned, of which a cis-acting element is involved in the cell-specific transcription.

The transcription cis-acting element of MUC1 is derived from mammalian cells, including but not limited to human cells, and is preferably expressed in human cells. The transcription cis-acting element of MUC1 comprises all the 0.9 kb sequence of 5' end of MUC1 gene. It may also comprise the following sequences linked to a promoter (relative to the transcription initiation site): nt−725~nt+31, nt−743~nt+33, nt−750~nt+33, and nt−598~nt+485, etc.

Prostaglandin Specific Antigen Enhancer and Promoter

Prostaglandin specific antigen enhancer is located at nt−5322~nt−3739 from the transcription initiation site of prostaglandin specific antigen, and the promoter is located at nt−540~nt+12 from the transcription initiation site. Said promoter and enhancer are specifically activated in prostate cells and prostate cancer cells.

Vasodilatin Enhancer and Promoter

Said enhancer and promoter are specifically activated in prostate cells and prostate cancer cells.

The promoter may be selected from the following: Orip from Epstein-Barr virus (EB virus), FR of Orip from EB virus, Bam HI C-promoter from EB virus, Orip in combination with Bam HI-C promoter of EB virus, FR of Orip from EB virus in combination with the essential promoter of herpes simplex virus thymidine kinase or SV40 essential promoter, the cis-acting element specifically activated in EB infected or latently infected cells.

In one embodiment, the invention provides a recombinant virus, wherein the transcription of at least one VPEG in the genome is under the control of a telomerase promoter, and some other VPEGs are deficient in functions, while the recombinant can still propagate specifically in tumor cells. Said deficiency in functions may be carried out through point mutations(s), deletions(s) and/or insertion(s) in the coding gene, or resulted from naturally-occurring mutations.

In one embodiment, the virus is a recombinant adenovirus, wherein the function of E1B 55 kDa protein is abnormal due to point mutations(s), deletions(s) and/or insertions(s).

In another embodiment, the virus is a recombinant adenovirus, wherein the function of E1B 19 kDa protein is abnormal due to point mutations, deletions and/or insertions.

In one embodiment, the virus is a recombinant adenovirus, wherein the function of E1A protein is abnormal due to point mutations, deletions and/or insertions.

In one embodiment, the virus is a recombinant herpes simplex virus, wherein the function of ICP6 protein is abnormal due to point mutations, deletions and/or insertions.

In one embodiment, the virus is a recombinant herpes simplex virus, wherein the function of two-copy ICP34.5 protein is abnormal due to point mutations, deletions and/or insertions.

The invention also provides a method for the proliferation of a recombinant virus, comprising infecting the telomerase activity positive host cells with the recombinant virus (e.g. the recombinant adenovirus), whereby the recombinant virus specifically propagating in said cells.

The telomerase activity positive cells will be specifically killed when infected by an adenovirus which only propagates in said cells. When the modified virus is mixed with a cell mixture in vivo or in vitro, it only propagates in telomerase activity positive cells. In other words, telomerase activity negative cells will not be killed by this adenovirus. Due to the proliferation and propagation of adenovirus, the telomerase activity positive cells among the cell mixture will be killed. Once the target cells are killed, the adenovirus will not propagate any more.

The invention provides the specific application of said recombinant virus. For example, said recombinant virus (e.g. a recombinant adenovirus) can be used to infect telomerase activity positive tumor cells, whereby inducing cyto toxicity, or be used to inhibit the growth of telomerase activity positive tumor cells, or be used to selectively kill telomerase activity positive tumor cells in vivo.

Various means are available for delivering the recombinant virus to target cells, including but not limited to liposome, conventional transfection method (e.g. calcium phosphate precipitation or electroporation), direct injection and intravenous infusion. The selection of the delivering means mainly depends on the particular recombinant virus used (such as its morphology) and the type and location of the target cells (i.e. whether the cells are in vitro or in vivo).

If a packaged recombinant virus is used, it can be administered at a dose of about $10^4$ to about $10^{14}$ in a physiologically acceptable carrier. The multiplicity of infection is generally in the range of 0.001-100. If administered as a polynucleotide (i.e. not packaged into virus), its dosage can be in the range of about 0.01 ug to about 1000 ug. The specific dosage can be determined based on the knowledge (available from the published documents) about the virus, and may also be empirically determined. The recombinant virus can be administered in one or more times, which depends on the desired use and the immune response capability of the subject. It may also be administered as multiple injections. If a immune response is not desirable, various immunosuppressants are available to suppress the immune response, so that a strong immune response will not be induced upon repeated administration.

The invention further provides a composition containing the recombinant virus of the present invention, such as a pharmaceutical composition. Such composition may be administered in vivo. Preferably, the composition further comprises a pharmaceutically acceptable excipient. These compositions, which comprise an effective amount of the recombinant virus of the present invention in combination with a pharmaceutically acceptable excipient, can be generally administered to the subject in a single dose form aseptic solution or suspension for parenteral administration, aseptic solution or suspension for non-parenteral or oral administration, oil-in-water emulsion or water-in-oil emulsion. The parenteral or non-parenteral administration is well known in the art, and may refer to Remington's Pharmaceutical Science, 18$^{th}$, Mack Publishing (1990). The pharmaceutical composition also comprises a lyophilized form and/or reconstructed form of the recombinant virus according to this invention.

The invention also provides a therapy method, comprising administering an effective amount of the recombinant virus according to the invention to a subject. Said method can be used either to treat tumor (i.e. liver cancer) patients, or to treat tumor high risk group, such as those that have family history of such disease, or have been cut off a tumor or been treated in other ways (i.e. chemotherapy). Whether or not to apply the recombinant virus according to the invention will in particular rely on some appreciable clinical parameters, such as serological index and biopsy. A pharmaceutical composition comprising the recombinant virus is generally administered, wherein the pharmaceutical composition is described as above.

The amount of recombinant virus to be administered is determined by various factors, such as the specific type of the recombinant virus, route of administration, the condition of the individual, the severity of disease and the particular cancer therapeutic gene.

If administered as a packaged recombinant virus, about $10^4$ to about $10^{14}$, preferably about $10^4$ to about $10^{12}$, more preferably about $10^4$ to about $10^{10}$ is used. If administered as a polynucleotide, about 0.01 ug to about 100 ug can be administered, preferably 0.1 ug to about 500 ug, more preferably about 0.5 ug to about 200 ug. More than one recombinant virus may be administered either simultaneously or sequentially. Administrations are typically given periodically, while monitoring any response of the subject. It may be administered for example by intratumorally, intravenously or intraperitoneally.

The recombinant virus of the invention can be administered alone, or in combination with other active agents for example chemotherapeutic agent, such as cisplatin, 5-fluorouracil, mitomycin C, carbo platin, cyclophosphamide), which promote to achieve the desired aim.

The present invention has some advantages over the tumor therapy known in the prior art. The present invention employs a telomerase promoter to control the transcription of at least one VPEG, as well as a cancer therapeutic gene inserted in the viral genome. Thereby the virus can replicate and propagate specifically in telomerase activity positive tumor cells, resulting in high titre of virus to directly disrupt the tumor cell. Meanwhile, the cancer therapeutic gene is highly expressed in tumor cells upon the replication of virus, killing the telomerase activity negative tumor cells synergistically. The invention further employs a tumor-activated cis-acting element to control another VPEG, or renders a viral essential gene deficient in functions through gene mutation. Thus the virus is not able to replicate and propagate in human germ cell, hemopoietic stem cell and diverticulum cell in the gastrointestinal tract, further reducing the toxicity to normal cells. Moreover, the present invention is more efficient than the gene therapy that only employs a cancer therapeutic gene or that only employs a specifically proliferating virus.

EMBODIMENT OF THE INVENTION

Human adenoviruses are divided into six subgenuses, which are A, B, C, D, E and F, respectively. They are different in their ectotropism to host cells, tumorigenicity and pathogenic history. The invention is exemplified by adenovirus C type 5 (Ad5), but is not limited to it. The constructing methods of the invention are all conventional to those skilled in the art.

EXAMPLE 1

Construction of a Cloning Vector Comprising a hTERT Promoter

The genomic DNA is extracted from a fresh liver tissue of normal human body, and the hTERT promoter is amplified using nested PCR (referring to PCR Protocols Current Methods and Applications, Ed. by White B A, Humana Press Inc., 1993). Three restriction sites respectively for EcoR I, Not I and Bgl I are inserted to 5' end of the promoter, while two restriction sites respectively for Swa I and BamH I are inserted to 3' end.

```
Primer 1:
5' CGG GCT CCC AGT GGA TTC 3';        (SEQ ID NO: 1)

Primer 2:
5' AAC GTG GCC AGC GGC AGC ACC TC     (SEQ ID NO: 2)

3';

Primer 3:
5' GGA ATT CGC GGC CGC AGA TCT CAC    (SEQ ID NO: 3)

AGA CGC CCA GGA ACC 3';

Primer 4:
5' CGG GAT CCA TTT AAA TTG GCC GGG    (SEQ ID NO: 4)

GCC AGG GCT TC 3'.
```

A first PCR amplification is carried out using primer 1 and primer 2, and a fragment of 370 bp is recovered. Then a second PCR amplification is performed on the 370 bp fragment using primer 3 and primer 4, resulting in a 270 bp fragment, which is recovered and subsequently cleaved by EcoR I and BamH I. The resulting fragment is then inserted into pUC19 vector (available from ATCC Company, USA) and sequenced. The sequence is as follows:

```
                                      (SEQ ID NO: 5)
5' gaattcgcgg ccgcagatct cacagacgcc caggaccgcg cttcccacgt ggcggaggga ctggggaccc gggcacccgt cctgcccctt caccttccag ctccgcctcc tccgcgcgga ccccgcccg tcccgacccc tcccgggtcc ccggcccagc cccctccggg ccctcccagc ccctcccctt cctttccgcg gccccgccct ctcctcgcgg cgcgagtttc aggcagcgct gcgtcctgct gcgcacgtgg gaagccctgg ccccggccaa tttaaatgga tcc 3'
```

The result shows that the sequence of hTERT promoter is correct, and thus the above resulting vector is named as pUC-hTERTp.

Synthesis of a linker containing 3×E-box.

```
Primer 5:
5' TCG AGG ACG CAC GTG GCG GCA CGT    (SEQ ID NO: 6)

GGG CGC ACG TGG GAT TTA AAT A 3';
```

```
-continued
Primer 6:
5' AGC TTA TTT AAA TCC CAC GTG CGC    (SEQ ID NO: 7)
CCA CGT GCG CCC ACG TGC GCC T 3'.
```

Primer 5 and primer 6 are denatured, renatured, and phosphorylated by a phosphokinase. Then they are inserted into pUC-hTERTp between Xho I and Hind III sites (referring to Molecular Cloning: A laboratory manual, 2th edition, J. Sambrook, Scientific Press, 1996). The resulting plasmid is sequenced, and the sequence result is as follows:

```
                                          (SEQ ID NO: 8)
5' gaattcgcgg ccgcagatct cacagacgcc caggaccgcg cttcccacgt ggcggaggga ctggggaccc gggcacccgt cctgcccctt caccttccag ctccgcctcc tccgcgcgga ccccgcccg tcccgacccc tcccgggtcc ccggcccagc cccctccggg ccctcccagc ccctcccctt cctttccgcg gccccgccct ctcctcgcgg cgcgagtttc aggcagcgct gcgtcctgct gcgcacgtgg gaagccctgg ccccggccac tcgacgcacg tgggcgcacg tgggcgcacg tgggatttaa ataagct 3'
```

The results show that the sequence of hTERT promoter plus 3× E-box is correct. The above resulting plasmid is named as pUC-hTERT-Ep. Said hTERT promoter contains nt–213 to nt+47 of human hTERT promoter, with three E-box sequences incorporated downstream thereto. Said hTERT promoter further comprises a Not I and a Bgl II site inserted upstream, and a Swa I site inserted downstream, of said promoter.

EXAMPLE 2

Construction of an Attenuated Proliferating Adenoviral Vector Comprising hTERT Promoter to Control the Expression of E1A pXC.1 vector is available from Microbix Biosystem Inc. (Toronto, Canada), which comprises the sequence of bp22-5790 from adenovirus type 5. Seven unique restriction sites are created at bp552 in said vector, which corresponds respectively to Age I, Bst BI, Not I, Spe I, Sal I, Xho I and Swa I. Said sites are located 12 bp upstream of the start codon of E1A. The method used is site directed double PCR mutagenesis (referring to PCR Protocols Current Methods and Applications, Ed. White B A, Humana Press Inc., 1993), and the primers used are as follows:

Primer 7 (forward primer, comprising a EcoR I site): 5' TTC AAG AAT TCT CAT GTT TG 3' (SEQ ID NO:9);

Primer 8 (reverse primer, at the 5' end was added ATT TAA ATC TCG AGT CGA CAC TAG TGC GGC CGC TTC GAA CCG GT)5' ATT TAA ATC TCG AGT CGA CAC TAG TGC GGC CGC TTC GAG CCG GTG TCG AGC GGC TCG GA 3' (SEQ ID NO; 10);

Primer 9 (forward primer, at the 5' end was added ACC GGT TCG AAG CGG CCG CAC TAG TGT CGA CTC GAG ATT TAA ATC CGG)5' ACC GGT TCG AAG CGG CCG CAC TAG TGT CGA CTC GAG ATT TAA ATC CGG TGA CTG AAA ATG AGA CAT ATT A 3' (SEQ ID NO:11);

Primer 10 (reverse primer, comprising a Xba I site) 5' TTC TCT AGA CAC AGG TGA TG3' (SEQ ID NO:12).

The product of site directed double PCR mutagenesis is inserted into pGEM-T-easy vector according to the protocols provided by Promega Company. The resulting product is named as pGEM-T-E1° a., and sequenced. The results show that the sequence is identical to that in pXC.1, except that, at bp552 of pXC.1 was inserted a sequence (TTC GAA GCC GCC GCA CTA GTG TCG ACT CGA GAT TTA AAT CCG GT) (SEQ ID NO:28), whereby seven new restriction sites for Age I, Bst BI, Not I, Spe I, Sal I, Xho I and Swa I being created. The plasmids pGEM-T-E1A and pXC.1 are cleaved by EcoR I and Xba I. The fragment cleaved from pGEM-T-E1A is inserted into pXC.1 between the EcoR I and Xba I sites. Thus at bp552 was inserted a sequence (ITC GAA GCG GCC GCA CTA GTG TCG ACT CGA GAM TTA AAT CCG GT) (SEQ ID NO:28), whereby seven new restriction sites for Age I, Bst BI, Not I, Spe I, Sal I, Xho I and Swa I being created. Said sites are located 12 bp upstream of the start codon of E1 A, and the resulting plasmid is named as pQW1.

pUC-hTERTp is cleaved by Not I and Swa I, and the fragment is inserted into pQW1 between the Not I and Swa I sites. A fragment of 1310 bp is amplified by PCR using primers 4 and 7. This demonstrates that the hTERT promoter has been inserted into pQW1 in a forward orientation between the Not I and Swa I sites, i.e. at bp12 upstream of the start codon of E1A of adenovirus type 5. The plasmid constructed as above is named as pQW-hTERTp. pUC-hTERT-Ep is cleaved by Not I and Swa I, and the fragment is inserted into pQW1 between the Not I and Swa I sites. A fragment of 1352 bp is amplified by PCR using primers 6 and 7. This demonstrates that the hTERT promoter plus three E-box sequences downstream of the transcription initiation site has been inserted into pQW1 in a forward orientation between Not I and Swa I sites, i.e. at bp12 upstream of the start codon of E1A of adenovirus type 5. The plasmid constructed as above is named as pQW-hTER-Ep.

EXAMPLE 3

Construction of an Attenuated Reproductive Adenovirus Comprising hTERT Promoter and Hypoxia Response Element Controlling the Expression of E1 A and E1B Respectively The hypoxia response element (HRE) in combination with human minimal cytomegalovirus promoter (mini-CMVp) is consisted of five copies of HRE and a human minimal cytomegalovirus promoter. Said HRE is derived from the promoter of vascular endothelial growth factor, and the sequence of the five copies of HRE is as follows:

```
                                          (SEQ ID NO: 13)
5'

CCA CAG TGC ATA CGT GGG CTC CAA CAG GTC CTC TT CCA

CAG TGC ATA CGT GGG CTC CAA CAG GTC CTC TT CCA CAG

TGC ATA CGT GGG CTC CAA CAG GTC CTC TT CCA CAG TGC

ATA CGT GGG CTC CAA CAG GTC CTC TT CCA CAG TGC ATA

CGT GGG CTC CAA CAG GTC CTC TT 3'
```

The sequence of the human minimal cytomegalovirus promoter (mini-CMVp) is as follows:

(SEQ ID NO: 14)
5' GGT AGG CGT GTA CGG TGG GAG GTC TAT ATA AGC AGA GCT CGT TTA GTG AAC CGT CAG ATC 3'

The hypoxia response element (HRE) in combination with human minimal cytomegalovirus promoter (mini-CMVp) comprises, besides the above two sequences, Spe I sites at 5' end and 3' end. It was synthesized by Shenneng Bocai Biotechnology LTD. (Shanghai, China), It is named as pMD-HRE. The sequence is verified through sequencing, and listed as follows:

(SEQ ID NO: 15)
5'
ACTAGTCCACAGTGCATACGTGGGCTCCAACAGGTCCTCTTCCACAGTG
CATACGTGGGCTCCAACAGGTCCTCTTCACAGTGCATACGTGGGCTCCA
ACAGGTCCTCTTCCACAGTGCATACGTGGGCTCCAACAGGTCCTCTTCCA
CAGTGCATACGTGGGCTCCAACAGGTCCTCTTGGTAGGCGTGTACGGTG
GGAGGTCTATATAAGCAGAGCTCGTTTAGTGAACCGTCAGATCACTAGT
3'

The E1B promoter located between nt1926 and nt2043 (i.e.nt1595-nt1713 of adenovirus type 5) of plasmid pQW-hTER-Ep is deleted. A new and unique Spe I site is generated at said deleted location through site directed double PCR mutagenesis (referring to PCR Protocols Current Methods and Applications, White B A edits, Humana Press Inc., 1993), which is located 4 bp upstream of the start codon of E1B. The primers used in the site directed double PCR mutagenesis are as follows:

Primer 11:
5' TCA CCT GTG TCT AGA GAA TGC 3' (SEQ ID NO: 16)

Primer 12:
5' CTC CCA AGC CTC CAT ACT AGT TTA (SEQ ID NO: 17)
AAC ATT ATC TCA CCC TTT 3'

Primer 13:
5' ACT AGT ATG GAG CTT GGG AGT GTT (SEQ ID NO: 18)
TTG 3'

Primer 14:
5' GGC CAG AAA ATC CAG CAG GTA 3' (SEQ ID NO: 19)

The PCR product is inserted into pGEM-T-easy vector according to the protocol provided by Promega, and the resulting plasmid is named as pGEM-T-E1B. Said plasmid is sequenced, and the results show that, the sequence of pGEM-T-E1B is identical to that of pQW-hTER-Ep, except that nt1926-nt2043 is deleted in pQw-hTER-Ep and replaced with a new Spe I site. The plasmids pGEM-T-E1B and pQW-hTER-Ep are cleaved by Kpn I and Xba I. The fragment cleaved from pGEM-T-E1B is inserted into pQW-hTER-Ep between the Kpn I and Xba I sites, whereby nt1926-nt2043 of pQW-hTER-Ep is deleted and replaced with a new Spe I site. Said Spe I site is located 4 bp upstream of the start codon of E1B. Said plasmid is named as pQW2-Spe.

The pMD-HRE is cleaved by Spe I. The fragment containing hypoxia response element (HRE) in combination with human minimal cytomegalovirus promoter (mini-CMVp) is recovered, and inserted into pQW2-Spe plasmid in the Spe I site. The orientation of the inserted fragment is verified through PCR.

Primer 15:
5' AGG TCT ATA TAA GCA GAG CTC 3' (SEQ ID NO: 20)

PCR is performed using primers 14 and 15, resulting in a fragment of 518 bp. This demonstrates that hypoxia response element (HRE) in combination with human minimal cytomegalovirus promoter (mini-CMVp) is inserted in a forward orientalion upstream of E1B. The plasmid constructed as above is named as pQW-hTERT-Ep-HRE.

EXAMPLE 4

Recombination of an Attenuated Reproductive Adenovirus Under the Control of hTERT The cell line 293 is available from Microbix Biosystem Inc. (Toronto, Canada), which is resulted from the transformation of human fetal kidney cells by the cleaved adenovirus type 5. The cell line 293 comprises and expresses the E1 region of adenovirus type 5, and can be effectively transfected by adenovirus DNA. The cell line 293 is co-transfected by a plasmid containing the left arm of adenovirus DNA in combination with a plasmid containing the right arm of adenovirus DNA to produce an infective adenovirus through homologous recombination. Using Lipofectamine, the cell line 293 is co-transfected by a plasmid pBHGE3 containing the right arm of adenovirus DNA in combination with each of pQW-hTERTp, pQW-hTERT-Ep and Adv-hTERT-Ep-HRE (referring to the specification of GIBCO BRL Company). The pBGHE3 is available from Microbix Biosystem Inc. (Toronto, Canada), which comprises the right arm of adenovirus DNA and E3 region. Virus plaques occur 9-14 days after cotransfection. Upon three purification of the virus plaques, the adenoviruses where M1A is under the control of hTERT are obtained, and named respectively as Adv-hTERTp-E1a (QW1), Adv-hTERT-Ep-E1a (QW2) and Adv-hTERT-Ep-E1a-HRE-E1b (QW3), referring to FIG. 1.

The recombinant virus as described above is listed in the following table:

| Virus | Name | Plasmid containing the Left arm of Ad5 DNA | Plasmid containing the Right arm of Ad5 DNA |
|---|---|---|---|
| Adv-hTERTp-E1a | QW1 | pQW-hTERTp | PBHGE3 |
| Adv-hTERT-Ep-E1a | QW2 | pQW-hTERT-Ep | PBHGE3 |
| Adv-hTERT-Ep-E1a-HRE-E1b | QW3 | pQW-hTERT-Ep-HRE | PBHGE3 |

Adenovirus propagates to a high level in the 293 cell line, and is then purified through $CsCl_2$ gradient centrifugation (refer to Molecular Cloning: A laboratory manual, 2th edition, J. Sambrook, Science Press, 1996).

The sequence of Adv-hTERTp-E1a (QW1) is identical to that of adenovirus type 5, except that a hTERT promoter is inserted between the transcription initiation site and the translation initiation site of E1A.

The sequence of Adv-hTERT-Ep-E1a (QW2) is identical to that of adenovirus type 5, except that a hTERT promoter and three copies of E-box are inserted between the transcription initiation site and the translation initiation site of E1A.

The sequence of Adv-hTERT-Ep-E1a-HRE-E1b (QW3) is identical to that of adenovirus type 5, except that, a hTERT promoter and three copies of E-box are inserted between the transcription initiation site and the translation initiation site of E1A, the E1B promoter is deleted, and five copies of HRE-mini-CMVp are inserted upstream of E1 B.

EXAMPLE 5

Figure 2:
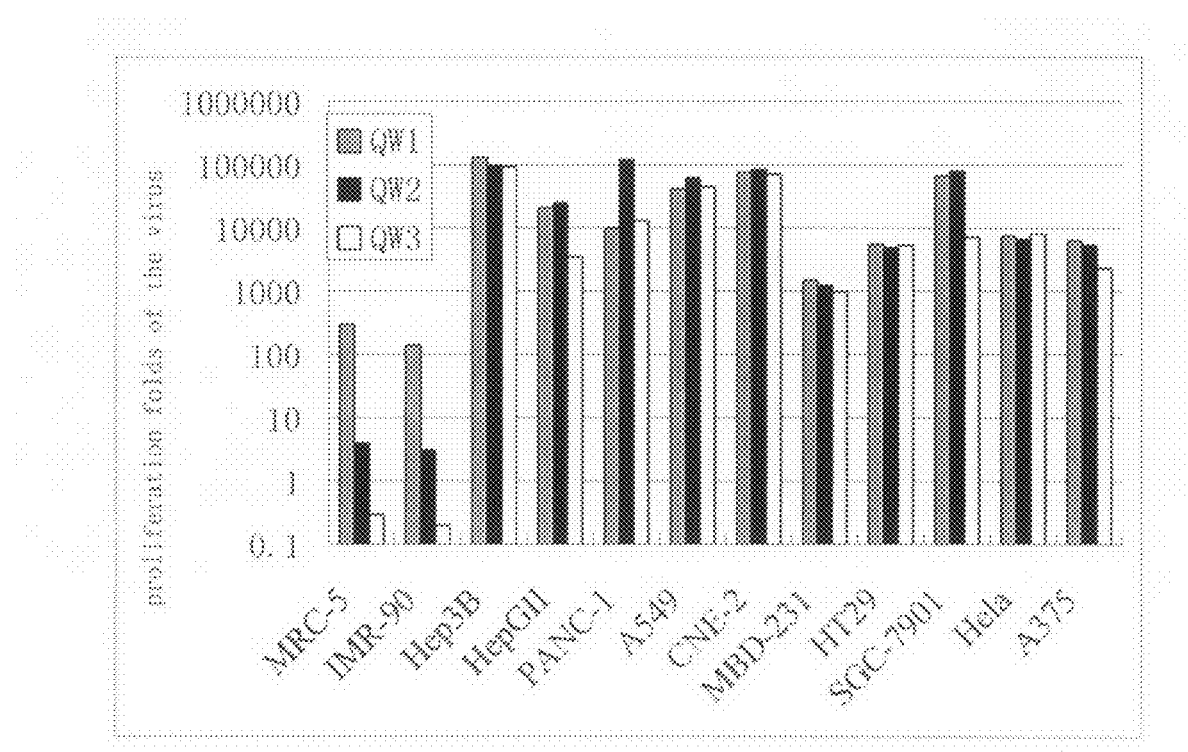
FIG. 2 shows the proliferation folds of QW1, QW2 and QW3 in normal and tumor cell lines after 48 hr.

Proliferation Ability Comparison of an Attenuated Reproductive Adenovirus (Wherein the Expression of E1A is Under the Control of hTERT Promoter) in Normal and Tumor Cell Lines The normal lung fibroblasts MRC-5 and IMR-90 are negative in telomerase activity. The tumor cell lines include liver cancer cell lines (Hep GII and Hep3B), breast cancer cell line (MRD-231), lung cancer cell line (A549), melanoma cell line (A375), colon cell line (HT29), pancreas carcinoma cell line (Panc-1), cervical carcinoma cell line (Hela), nasopharyngeal carcinoma cell line (CNE-2) and gastric carcinoma cell line (SGC7901). Among the above cell lines, CNE-2 and SGC7901 are available from Institute of Cell Biology, Chinese Academy of Science, while others are from ATCC Company (USA). Said tumor cell lines are all positive in telomerase activity. Cell lines are plated on 6-well plates at a density of $5 \times 10^5$ cells/well, and cultured in a 37C incubator (5% $CO_2$). They are refreshed with 1 mL serum-free culture medium on the next day, and QW1, QW2 or QW3 are added thereto respectively at a level of $2.5 \times 10^6$/well. After incubation for 90 min, the viruses inoculated are removed through two washes in PBS. The cells are then cultured in a medium with a supplement of 5% fetal calf serum. At 0 and 48 hr after infection, the cells are harvested, lysed by three cycles of freeze-thaw, and titred by TCID50 method (referring to AdEasy™ manual of Qbiogene Company, USA). The results show that, the proliferation capability of the viruses in normal cells is QW3<QW2<QW1, while their proliferation capability is almost the same in tumor cell lines (see FIG. 2).

Figure 3:
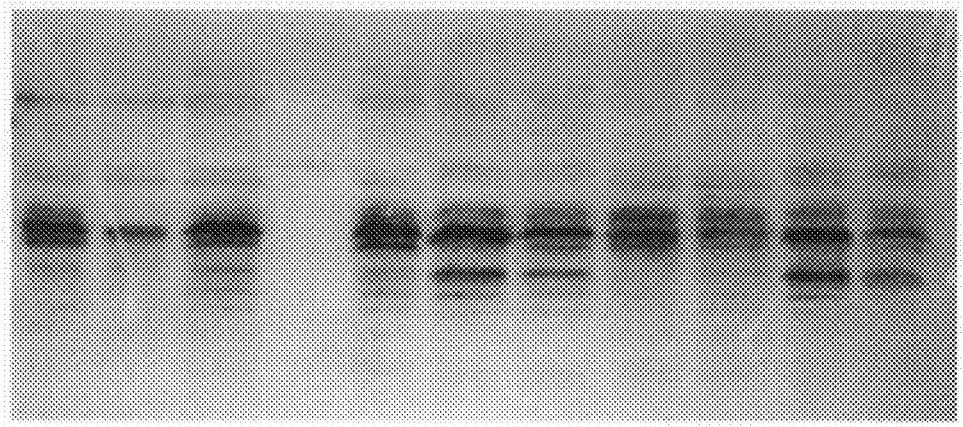
FIG. 3 shows the expression levels of E1A by QW2(the attenuated reproductive adenovirus comprising a hTERT promoter and three copies of E-box sequence incorporated downstream thereof to control the expression of E1A) in normal cells and tumor cell lines.

Western Blot (referring to Molecular Cloning: A laboratory manual, 2th edition, J. Sambrook, Science Press, 1996) shows that E1A of QW2 is not expressed in either of the normal cell lines MRC-5 and IMR-90, while is highly expressed in the tumor cell lines A549, Hep 3B and Panc-1 (see FIG. 3).

EXAMPLE 6

Construction of an Adenovirus Vector which Comprises a Human Endostatin Gene and a Deletion of E1 Region The vector pCA13 is available from Microbix Biosystem Inc. (Toronto, Canada), which comprises a sequence of bp22-5790 from adenovirus type 5. In pCA13, bp342-3523 of E1 region is deleted and replaced with a human minimal cytomegalovirus (HCMV) IE promoter (−299~+72) and SV40 polyA tailing signal. Human endostatin is amplified through PCR as follows: total RNA is extracted from fresh liver tissue of normal human and is reverse transcribed with random primers. Through double PCR technique (referring to PCR Protocols Current Methods and Applications, Ed. White B A, Humana Press Inc., 1993), the signal peptide of Oncostatin-M is introduced upstream of the endostatin gene, with two restriction sites for EcoR I and Xba I are inserted upstream of said signal peptide and down stream of said gene.

```
Primer 16:
5' GGG GAA TTC ACC ATG GGG GTA CTG (SEQ ID NO: 21)

CTC ACA CAG AGG ACG CTG CTC AGT

CTG GTC CTT GCA CTC 3';

Primer 17:
5' CTG CTC AGT CTG GTC CTT GCA CTC (SEQ ID NO: 22)

CTG TTT CCA AGC ATG GCG AGC CAC

CGC GAC TTC CAG 3';

Primer 18:
5' GCT CTA GAC TAT TAC TTG GAG GCA (SEQ ID NO: 23)

GTC ATG AAG CTG TTC TCA ATG CAT

AGC ACG ATG TAG GCG TG 3'.
```

A first PCR amplification is performed by using primers 17 and 18, and a fragment of 615 bp is recovered, which is subsequently amplified by a second PCR using primers 16 and 18. A fragment of 647 bp is recovered, and then cleaved by EcoR I and Xba I. The cleaved fragment is then inserted into pbluescript IIKS (+) vector (purchased from ATCC Company, USA), and sequenced. The results are as follows:

```
                                            (SEQ ID NO:24)
5'
GAATTCACCATGGGGGTACTGCTCACACAGAGGACGCTGCTCAGTCTGGTC

CTTGCACTCCTGTTTCCAAGCATGGCGAGCCACAGCCACCGCGACTTCCAG

CCGGTGCTCCACCTGGTTGCGCTCAACAGCCCCCTGTCAGGCGGCATGCGG

GGCATCCGCGGGGCCGACTTCCAGTGCTTCCAGCAGGCGCGGGCCGTGGGG

CTGGCGGGCACCTTCCGCGCCTTCCTGTCCTCGCGCCTGCAGGACCTGTAC

AGCATCGTGCGCCGTGCCGACCGCGCAGCCGTGCCCATCGTCAACCTCAAG

GACGAGCTGCTGTTTCCCAGCTGGGAGGCTCTGTTCTCAGGCTCTGAGGGT

CCGCTGAAGCCCGGGGCACGCATCTTCTCCTTTAACGGCAAGGACGTCCTG

AGGCACCCCACCTGGCCCCAGAAGAGCGTGGAGCATGGCTCGGACCCCAAC

GGGCGCAGGCTGACCGAGAGCTACTGTGAGACGTGGCGGACGGAGGCTCCC

TCGGCCACGGGCCAGGCCTCCTCGCTGCTGGGGGGCAGGCTCCTGGGGCAG

AGTGCCGCGAGCTGCCATCACGCCTACATCGTGCTATGCATTGAGAACAGC

TTCATGACTGCCTCCAAGTAATAGTCTAG 3'.
```

The fragment is released by EcoR I and Xba I, and inserted into pCA13 vector in a directed orientation between the EcoR I and Xba I sites. The resulting vector is named as pCA13-human endostatin.

EXAMPLE 7

Construction of an Adenovirus Vector Comprising Endostatin Gene, with the Expression of E1A Under the Control of hTERT Promoter pCA13-human endostatin is cleaved by Bgl II. A fragment of 1237 bp (containing HCMV IE promoter (−299~+72), human endostatin with Oncostatin-M signal peptide and SV40 polyA tailing signal) is recovered, and then inserted into the Bgl II site of pUC-hTERTp. The insertion orientation is verified by PCR.

Primer 19(3' primer of hTERT promoter): 5' TGG CCG GGG CCA GGG CTT C 3' (SEQ ID NO:25)

Primer 20 (3' primer of human endostatin, located in bp577-600 of Oncostatin-M signal peptide and human endostatin): 5' AGC ACG ATG TAG GCG TGA TGG C 3' (SEQ ID NO:26).

A fragment of 1108 bp is amplified by primers 19 and 20, which demonstrates that HCMV IE promoter (−299~+72), human endostatin with Oncostatin-M signal peptide and SV40 polyA tailing signal are inserted in a forward orientation into the Bgl II site of pUC-hTERT-Ep. The resulting vector is named as pUC-hTERT-Ep-endostatin.

pUC-hTERT-Ep-endostatin is cleaved by Not I and Swa I, and the resulting fragment is inserted between Not I and Swa I sites of pQW-hTERT-Ep. The resulting vector is named as pQW-hTERT-Ep-endostatin.

EXAMPLE 8

Recombination of a Non-Reproductive Adenovirus Comprising Endostatin and a Reproductive Adenovirus Comprising Endostatin with the Expression of E1A Under the Control of hTERT Promoter The cell line 293 is available from Microbix Biosystem Inc. (Toronto, Canada), which is resulted from the transformation of human fetal kidney cells by the cleaved adenovirus type 5 DNA. The cell line 293 comprises and expresses the E1 region of adenovirus type 5, and can be effectively transfected by adenovirus DNA. The cell line 293 is co-transfected by a plasmid containing the left arm of adenovirus DNA in combination with a plasmid containing the right arm of adenovirus DNA, whereby an infective adenovirus being produced through homologous recombination. Using Lipofectamine, the cell line 293 is co-transfected by a plasmid pBHGE3 containing the right arm of adenovirus DNA respectively in combination with pCA13-endostatin and pQW-hTERT-Ep-endostatin (referring to the protocol of GIBCO BRL Company). pBGHE3 and pBHG10 are available from Microbix Biosystem Inc. (Ontario, Canada). pBGHE3 comprises the right arm of adenovirus type 5 DNA and E3 region, while pBGH10 comprises the right arm of adenovirus type 5 DNA with a deletion of the E3 region. The virus plaques occur 9-14 days after co-transfection. Upon three times of purification of the virus plaques, a non-reproductive adenovirus comprising endostatin are obtained and a reproductive adenoviruses comprising endostatin with E1A under the control of hTERT promoter are obtained, and named respectively as Ad-endostatin and Adv-hTERT-Ep-E1a-endostatin (QW2-endostatin).

The recombinant virus as described above is listed in the following table:

| Virus | Name | Plasmid containing the Left arm of Ad5 DNA | Plasmid containing the Right arm of Ad5 DNA |
|---|---|---|---|
| Ad-endostatin | Ad-endostatin | pCA 13-endostatin | PBHGE3 |
| Adv-hTERT-Ep-E1a-endostatin | QW2-endostatin | pQW-hTERT-Ep-endostatin | PBHGE3 |

After propagating to a high level in 293 cell line, the adenovirus is purified in a large scale by CsCl gradient centrifugation (referring to Molecular Cloning: A laboratory manual, 2th edition, J. Sambrook, Science Press, 1996). Ad-endostatin is a non-reproductive adenovirus type 5 which comprises human endostatin and a deletion of E1 region, i.e. a conventional adenovirus vector system comprising human endostatin. The sequence of QW2-endostatin is identical to that of adenovirus type 5, except that, a hTERT promoter is inserted between the transcription initiation site and the translation initiation site of E1A, a Bgl II site is introduced upstream of hTERT promoter, and a gene sequence comprising HCMV IE promoter (−299~+72), human endostatin with Oncostatin-M signal peptide and SV40 polyA tailing signal is inserted in a forward orientation into said Bgl II site.

EXAMPLE 9

Figure 4:
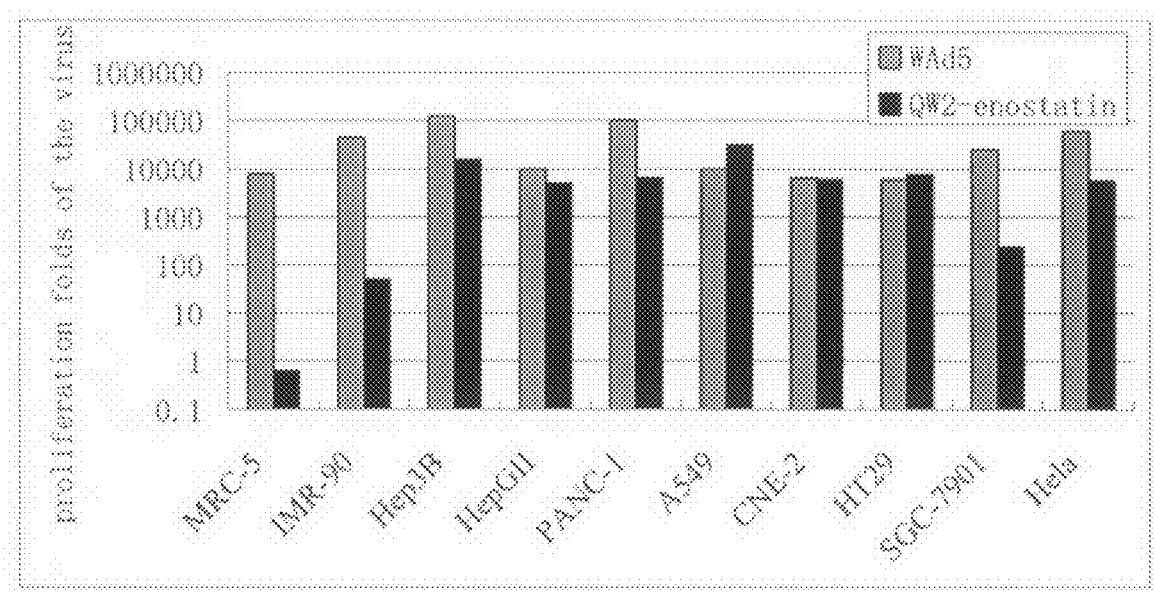
FIG. 4 compares the proliferation folds of the wild type adenovirus 5 (WAd5) and QW2-endostatin(the attenuated reproductive adenovirus comprising the endostatin gene, the hTERT promoter and three copies of E-box sequence incorporated downstream thereof to control the expression of E1A) after 48 hr's culturing in normal and tumor cell lines.

The Adenovirus Comprising Endostatin (Wherein the Expression of E1A is Under the Control of hTERT Promoter) Proliferates and Highly Expresses Human Endostatin in Telomerase Positive Tumor Cells In Vitro The normal cell lines, namely lung fibroblasts MRC-5 and IMR-90, are telomerase activity negative. The tumor cell lines include liver cancer cell lines (Hep GII and Hep3B), breast cancer cell line (MRD-231), lung cancer cell line (A549), melanoma cell line (A375), colon cell line (HT29), pancreas cancer cell line (Panc-1), cervical cancer cell line (Hela), nasopharyngeal carcinoma cell line (CNE-2) and gastric carcinoma cell line (SGC7901). Said cell lines are plated on 6-well plates at a density of $5 \times 10^5$ cells/well, and cultured in a 37° C. incubator (5% $CO_2$). They are refreshed with 1 mL serum-free culture medium on the next day, and adenovirus wild type 5(WAd5), Ad-endostatin and QW2-endostatin are added thereinto respectively at a level of $2.5 \times 10^6$/well. After an incubation of 90 min, the virus is washed away by two washes in PBS. The cells are then cultured in a medium with a supplement of 5% fetal calf serum and collected at 0 and 48 hr. The collected cells are freeze-thawed for three times, and titred by TCID50 method (referring to AdEasy™ manual of Qbiogene Company, USA). It can be seen that, WAd5 proliferates and propagates in both normal cells and tumor cells (referring to FIG. 4); Ad-endostatin proliferates and propagates in neither the normal cells nor the tumor cells; while QW2-endostatin propagates in the telomerase positive tumor cells, but not in normal cells which are negative in telomerase activity.

Figure 5:
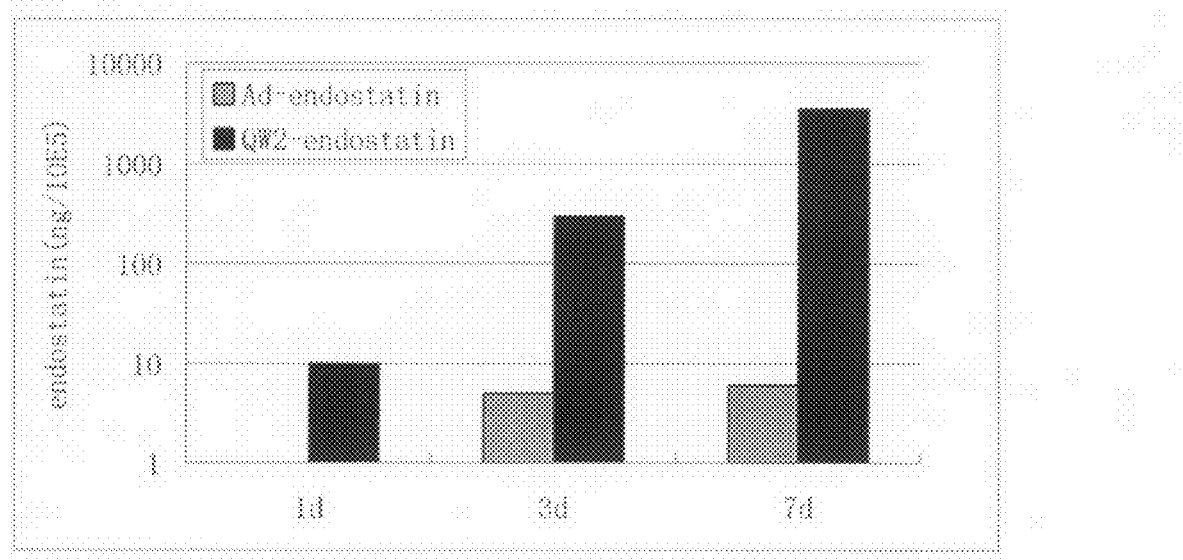
FIG. 5 compares the expression of the endostatin in tumor cell lines by QW2-endostatin(the attenuated reproductive adenovirus comprising the endostatin gene, the hTERT promoter and three copies of E-box sequence incorporated downstream thereof to control the expression of E1A) and Ad-endostatin(i.e. the non-reproductive adenovirus comprising a human endostatin gene).

The pancreas cancer cell line Panc-1 and the gastric carcinoma cell line SGC7901 are plated on 6-well plates at a level of $5 \times 10^5$ cells/well, and cultured in a 37° C. incubator (5% $CO_2$). They are refreshed with 1 mL serum-free liquid on the next day, and Ad-endostatin and QW2-endostatin are added thereto respectively at a level of $5 \times 10^5$/well. After an incubation of 90 min, the virus is washed away by two washes in PBS. The cells are then cultured in a medium with a supplement of 5% fetal calf serum, and collected at Day 0, 3 and 7. The results show that, the expression of endostatin in QW2-endostatin infected cells is substantively higher than that in Ad-endostatin infected cells (see FIG. 5)

The tumor cell line Hep 3B and the human normal fibroblasts are infected by QW2-endostatin with MOI of 1), and cultured at 37° C. for 1 hr. 7 days later, the cells are collected, and extracted for viral DNA using QIAamp DNA Blood mini kit (QIAGEN Company, German) according to the protocol provided by QIAGEN Company. The resulting DNA of QW2-endostatin is cleaved by Bgl II, subjected to electrophoresis on 1% agarose, and transferred to a nylon membrane. The cDNA fragment of human endostatin (a 637 bp fragment, derived from the cleavage of pCA13-human endostatin by EcoR I and Xba I) is $^{32}$P-labelled, and used as the probe to carry out Southern blotting. pCA13-human endostatin is used as a control of the copies of human endostatin (referring to Molecular Cloning: A laboratory manual, 2th edition, J. Sambrook, Science Press, 1996). The results show that, the copy number of human endostatin in the form of QW1-endostatin is $2 \times 10^4$ and <10 respectively in Hep 3B and human normal fibroblasts.

EXAMPLE 9

Figure 6:
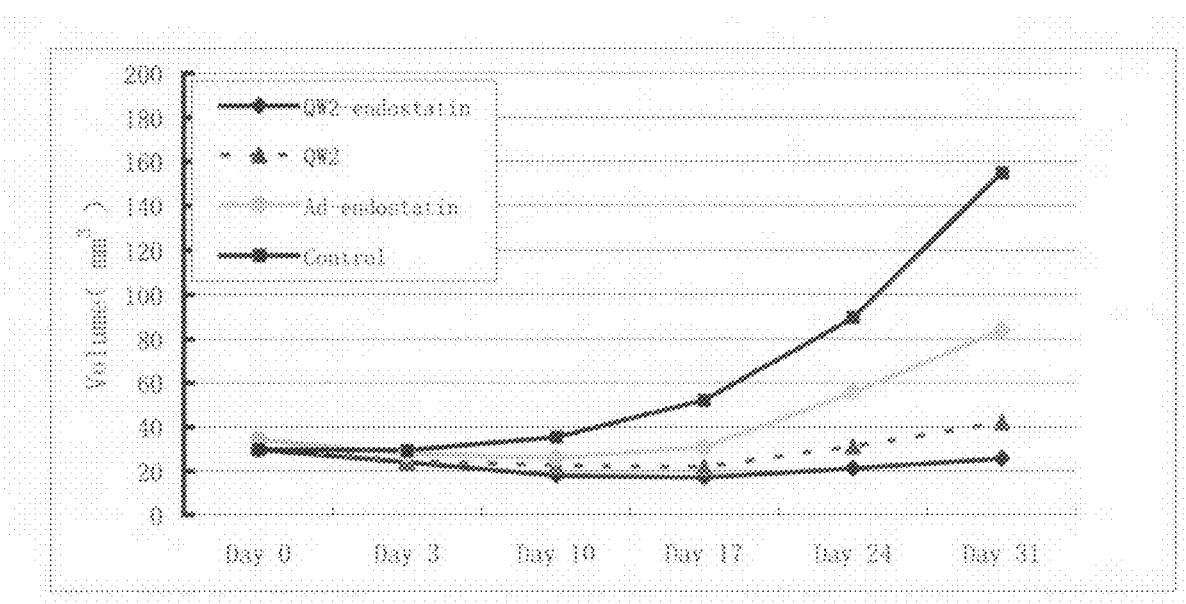
FIG. 6 compares the therapeutic effects of QW2(the attenuated reproductive adenovirus comprising the hTERT promoter and three copies of E-box sequence incorporated downstream thereof to control the expression of E1A), Ad-endostatin (i.e. the non-reproductive adenovirus comprising a human endostatin gene) and QW2-endostatin(the attenuated reproductive adenovirus comprising the endostatin gene, the hTERT promoter and three copies of E-box sequence incorporated downstream thereof to control the expression of E1A) on SCID mice into which Hep3B cells (human liver cancer cells) are transplanted.

Antitumor Effect of QW2-Endostatin in the Treatment of Transplanted Tumor in Nude Mouse 4-5 weeks old SCID mice are subcutenously inoculated with Hep 3B at a level of $1\times10^7$, and two weeks later, administered with QW2, Ad5-endostatin and QW2-endostatin for five times ($2\times10^8$ for each time) with a total dosage of $1\times10^9$. The results in FIG. 6 show that, four weeks later, the tumor size of the control group increases more than three times, while in the treated group, the tumor size shows little increase. The therapeutic effect of QW2-endostatin is better than that of QW2 and Ad5-endostatin.

The invention claimed is:

1. A recombinant virus, wherein the transcription of at least one virus proliferating essential gene (VPEG) of said virus is under the control of a telomerase promoter associated with a transcription initiation site, and the genome of said virus comprises a nucleotide sequence of a cancer therapeutic gene, wherein said telomerase promoter is an hTERT promoter, wherein multiple copies of an E-box as set forth in SEQ ID NO: 27 are introduced downstream of the transcription initiation site of the hTERT promoter, and wherein the recombinant virus is an adenovirus.

2. The recombinant virus according to claim 1, wherein at least one of said VPEGs is selected from the group of adenoviral early genes consisting of: the E1A gene, the E1B gene, the E2 gene and the E4 gene.

3. The recombinant virus according to claim 1, wherein at least one of said VPEGs is an adenoviral late gene.

4. The recombinant virus according to claim 1, wherein the cancer therapeutic gene is selected from the group consisting of a cancer suppressor gene; an antiangiogenic gene; a cytokine gene; a prodrug convertase gene; and an apoptosis gene.

5. The recombinant virus according to claim 4, wherein the cancer suppressor gene is selected from the group being consisted consisting of: a P53 gene, a P21 gene, an Rb gene, an NF1 gene, a VHL gene and an APC gene; the antiangiogenic gene is selected from the group consisting of an endostatin gene, an angiogenesis inhibitor gene, a kringle 1-4 structure gene, a kringle 1-5 structure gene, a kringle 1-3 structure gene and a kringle 1-5 structure gene plus a kringle 1-3 structure gene of plasminogen, an interferon-α gene, an interferon-β gene, an interferon-γ gene, a thrombospondin gene, a platelet cofactor 4 gene, a plasminogen activator inhibitor gene, an interleukin 12 gene, and a fibronectin gene; said cytokine gene is selected from the group consisting of: the interleukin 2 gene, an interleukin 12 gene, a granulocyte-monocyte colony stimulating factor gene, a tumor necrosis factor gene, an interferon α gene, an interferon β gene, an interferon γ gene, a Light gene, and a Flt3 ligand gene; said prodrug convertase gene is selected from the group consisting of: a herpes simplex virus thymidine kinase gene, a varicella-zoster virus thymidine kinase gene, and a E.coli cytosine deaminase gene; said apoptosis gene is selected from the group consisting of: the ICE gene, a capase-3 gene, capase-8 gene and capase-9 gene.

6. The recombinant virus according to claim 5, wherein the antiangiogenic gene comprises a sequence which encodes a secretory signal peptide.

7. The recombinant virus according to claim 6, wherein the secretory signal peptide is selected from the group consisting of: the signal peptide natively associated with the antiangiogenic gene, the signal peptide from Oncostatin-M and the signal peptide from immunoglobulin K chain.

8. The recombinant virus according to claim 1, wherein the recombinant virus has the following features: 1) transcription of another VPEG is under the control of a cis-acting element specifically activated in tumor cells; and/or 2) at least one VPEG is deficient in functions, while the virus can still specifically propagate in tumor cells.

9. The recombinant virus according to claim 8, wherein the transcription of another VPEG of said virus is under the control of at least one cis-acting element specifically activated in tumor cells, wherein said cis-acting element is selected from the group consisting of: a hypoxia response element, an S phase specific promoter, an α-fetoprotein enhancer and promoter, a carcino-embryonic antigen enhancer and promoter, a tyrosinase enhancer and promoter, a urokinase-type plasminogen activator enhancer and promoter, a ErbB2 enhancer and promoter, a ErbB3 enhancer and promoter, a ErbB4 enhancer and promoter, a DF3 breast cancer-associated antigen enhancer, a prostaglandin specific antigen enhancer and promoter, a vasodilatin enhancer and promoter, an Orip from EB virus, an FR enhancer of Orip from EB virus, and a Bam HI C-promoter of EB virus.

10. The recombinant virus according to claim 8, wherein the proteins encoded by the E1A gene, E1B55Kda gene and/or E1B19Kda are deficient in functions in said adenovirus.

11. A method for the proliferation of the recombinant virus according to claim 1, comprising in vitro infecting telomerase positive tumor cells with said recombinant virus, whereby causing cytotoxicity to said tumor cells.

12. A method of treating tumors in a mammal with the recombinant virus according to claim 1, comprising 1) infecting tumor cells in vivo with said virus thereby restricting the replication and proliferation of the virus essentially in tumor cells, causing increased copies of the nucleotide sequences encoding the cancer therapeutic gene as well as increased expression of the cancer therapeutic gene in tumor cells, thus specifically killing the tumor cells and inhibiting the formation, growth and metastasis of tumors.

13. The method according to claim 12, further comprising the step of administering a chemical antineoplastic agent before, during and/or after infecting the tumor cells with the recombinant virus according to claim 1.

14. A method for inhibition of tumor cell growth comprising administering to a subject the recombinant virus according to claim 1.

15. A pharmaceutical composition, comprising the recombinant virus according to claim 1 and a pharmaceutically acceptable carrier.

16. The method 12, wherein the mammal is a human.

\* \* \* \* \*